United States Patent
Lu

(10) Patent No.: US 10,188,312 B2
(45) Date of Patent: Jan. 29, 2019

(54) DETECTING HEAD DEVICE FOR CAPACITIVELY MEASURING AN ACUPUNCTURE POINT FREQUENCY OF A HUMAN BODY

(71) Applicant: Chin Hung Lu, Taipei (TW)

(72) Inventor: Chin Hung Lu, Taipei (TW)

(*) Notice: Subject to any disclaimer, the term of this patent is extended or adjusted under 35 U.S.C. 154(b) by 339 days.

(21) Appl. No.: 14/994,096

(22) Filed: Jan. 12, 2016

(65) Prior Publication Data
US 2016/0198974 A1    Jul. 14, 2016

Related U.S. Application Data

(60) Provisional application No. 62/102,119, filed on Jan. 12, 2015.

(51) Int. Cl.
*A61B 5/053*    (2006.01)

(52) U.S. Cl.
CPC ............ *A61B 5/053* (2013.01); *A61B 5/0532* (2013.01)

(58) Field of Classification Search
CPC ............................. A61B 5/053; A61B 5/0532
USPC ......................................................... 600/548
See application file for complete search history.

(56) References Cited

U.S. PATENT DOCUMENTS

| | | | |
|---|---|---|---|
| 4,516,179 A * | 5/1985 | Imakoshi | G11B 5/3106 324/252 |
| 5,643,173 A * | 7/1997 | Welles | A61M 21/00 600/26 |
| 2012/0143285 A1* | 6/2012 | Wang | A61B 5/024 607/59 |

\* cited by examiner

*Primary Examiner* — Daniel L Cerioni
(74) *Attorney, Agent, or Firm* — Hannah M. Tien

(57) ABSTRACT

The present invention provides a detecting head device for capacitively measuring an acupuncture point frequency of a human body, comprising: an internal oscillator, which generates a predetermined oscillation frequency; an electronic counter, which is connected to the internal oscillator and calculates an internal oscillation frequency; and an external interrupt security routine (ISR), which is connected to the counting module and calculates, in combination with the internal oscillation frequency, a frequency F2 of the contacted acupuncture point of the human body.

10 Claims, 3 Drawing Sheets

DETECTING HEAD DEVICE FOR CAPACITIVELY MEASURING AN ACUPUNCTURE POINT FREQUENCY OF A HUMAN BODY

FIELD OF THE INVENTION

The present invention relates to a detecting head device for capacitively measuring an acupuncture point frequency of a human body.

BACKGROUND OF THE INVENTION

The electrical status of various acupuncture meridians and acupuncture points reflects human health. According to electric circuit theories, detectable electric physical quantities are resistance, inductance and capacitance. It is known that the electrical resistance of human skin covering the entire body is from 100 K to 10 M ohms. Since the direct current resistance value needs be kept below 10 ohms when measuring the inductance, the electrical status of acupuncture meridians may not be determined by the measurement of inductance. The measurement of resistance is a possible way but affected by age, injuries, changes in weather conditions, and sweat production which change the direct current resistance. Physiological saline needs be applied to the measurement point to prevent errors. However, saline matters will corrode electronic devices and shortens the service lives of the measuring connectors when not appropriately maintained.

SUMMARY OF THE INVENTION

Figure 1A:
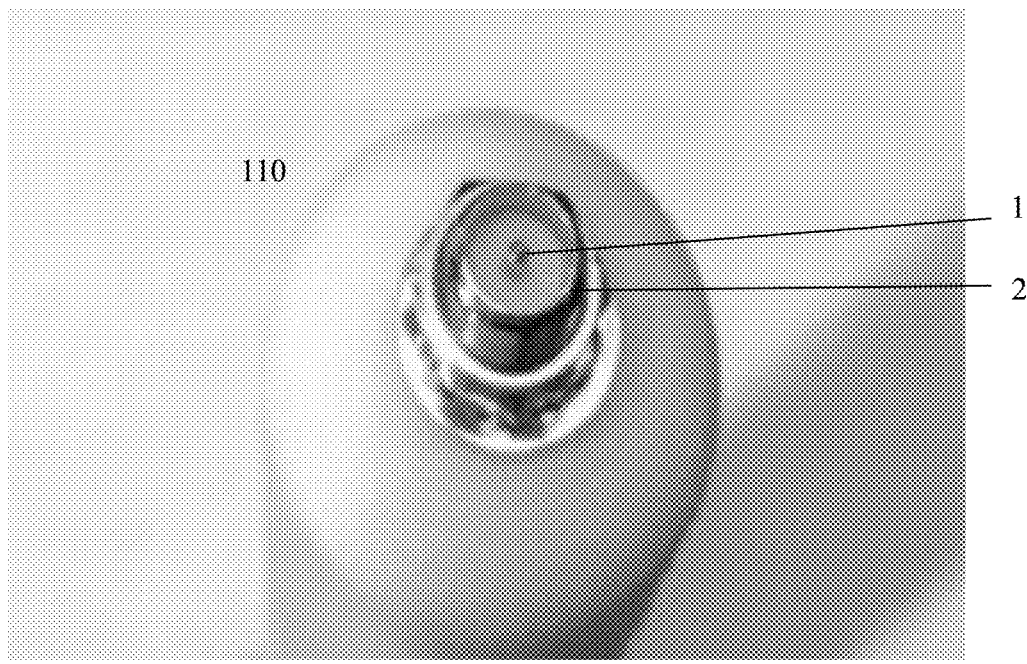
FIGS. 1A and 1B respectively show a structural diagram of a body-contacting contact head of a detecting head device for capacitively measuring an acupuncture point frequency of a human body.

The present invention provides a detecting head device for capacitively measuring an acupuncture point frequency of a human body, comprising: a contact head, which comprises two terminals and contacts with an acupuncture point of a human body to obtain a capacitance value CH of the acupuncture point, wherein one of two terminals is grounded; an internal oscillator, which comprises an inductor L1 and a capacitor C2 and generates a predetermined internal oscillation frequency F1; an electronic counter, which is connected to the internal oscillator and calculates the internal oscillation frequency; an external interrupt service routine (ISR), which is connected to the electronic counter and when the contact head contacts with an acupuncture point of a human body and the external interrupt service routine (ISR) receives an acupuncture point frequency signal from the contacted human body, the external interrupt service routine (ISR) calculates, in combination with the internal oscillation frequency, a frequency F2 of the contacted acupuncture point of the human body.

DETAILED DESCRIPTION OF THE INVENTION

In order to overcome many of the deficiencies in prior art and to build a database connecting to a cloud storage for further analysis and determination of human health conditions, the present invention provides a detecting head device for capacitively measuring an acupuncture point frequency of a human body, comprising: a contact head, which comprises two terminals and contacts with an acupuncture point of a human body to obtain a capacitance value CH of the acupuncture point, wherein one of two terminals is grounded; an internal oscillator, which comprises an inductor L1 and a capacitor C2 and generates a predetermined internal oscillation frequency F1; an electronic counter, which is connected to the internal oscillator and calculates the internal oscillation frequency; an external interrupt service routine (ISR), which is connected to the electronic counter and when the contact head contacts with an acupuncture point of a human body and the external interrupt service routine (ISR) receives an acupuncture point frequency signal from the contacted human body, the external interrupt service routine (ISR) calculates, in combination with the internal oscillation frequency, a frequency F2 of the contacted acupuncture point of the human body using mathematical formula shown as follows;

$$F2 = \frac{1}{2\sqrt{L1 \times (C2 + CH)}};$$

$$F1 = \frac{1}{2\sqrt{L1 \times C2}},$$

wherein F1 is an internal oscillation frequency of the internal oscillator, L1 and C2 are oscillatory elements of the internal oscillator, and CH is a capacitance value of the acupuncture point of the human body.

EXAMPLES

The present invention may be implemented in many different forms and should not be construed as limited to the examples set forth herein; The following detailed description is only used for representing the different examples and characters of the present invention, therefore, should not be construed as the limitation of the claims.

Figure 1B:
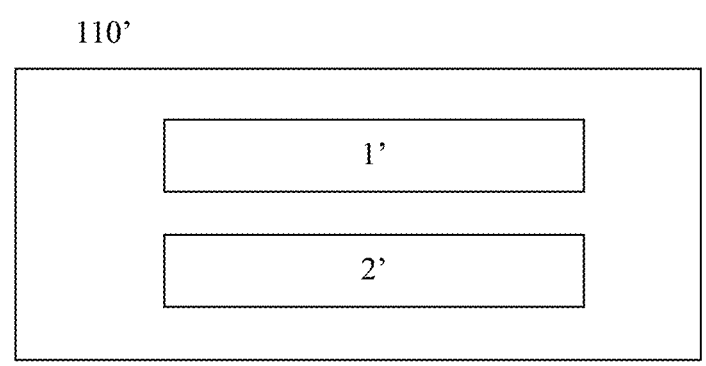

FIGS. 1A and 1B respectively show a structural diagram of a structurally different contact head of a detecting head device 100 for capacitively measuring the frequency of an acupuncture point of the human body. FIG. 1A shows a cylinder shaped contact head 110, wherein an terminal 1 contacts with an acupuncture point, and an terminal 2 is grounded. FIG. 1B shows a planar contact head 110', wherein an terminal 1' contacts with an acupuncture point, and an terminal 2' is grounded.

In addition, the material of the contact head includes, but is not limited to, a metal or an alloy, for example plated gold.

The present invention uses an 18k gold contact head to measure the capacitance, which determines physical quantities mainly through its electrical charge and discharge characteristics rather than direct measurement of electric currents passing through a human body to minimize the effects of factors influencing the skin resistance. Therefore, the present invention measures capacitance to obtain parameters of each acupuncture point. There are two methods of measuring the capacitance. The first method is to apply a fixed electric voltage to observe transient characteristics. The second method is to assemble an oscillator by combining suitable feedback circuits to measure an output frequency. The first method provides higher accuracy, but the size of the measuring device is rather large. The second method, when errors can be controlled below 5%, the size of the device can be reduced effectively. Therefore, the present invention adopts a method of generating a circuit by frequencies to measure a capacitance value of an acupuncture point of acupuncture meridians.

Figure 2:
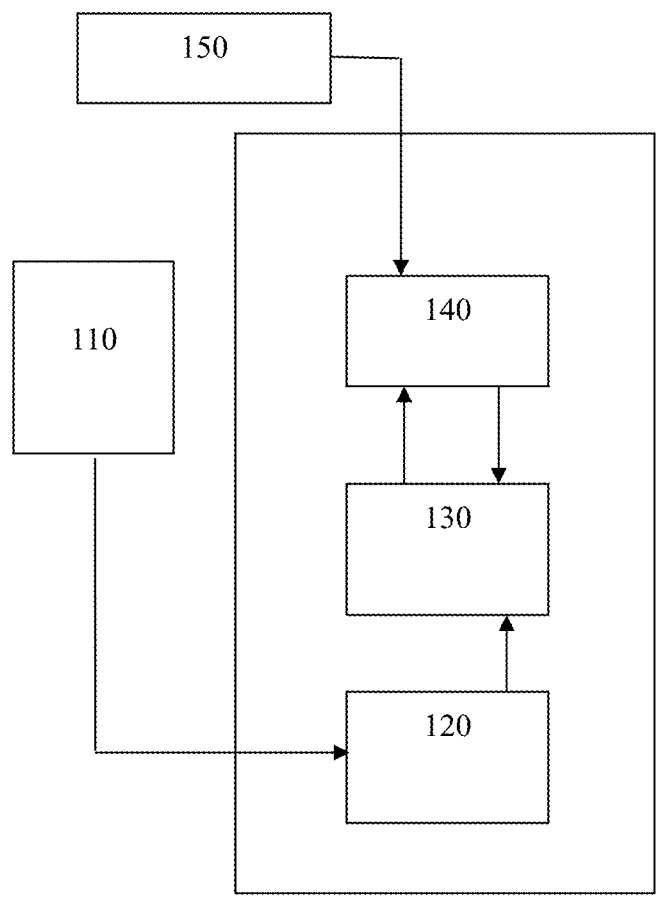
FIG. 2 shows a structural block diagram of a detecting head device for capacitively measuring an acupuncture point frequency of a human body.

FIG. 2 shows a structural block diagram of a detecting head device 100 for capacitively measuring an acupuncture point frequency of a human body, comprising: a contact head 100, shown in FIG. 1A, (also, a contact head 110', shown in FIG. 1B) which comprises two terminals (i.e. terminals 1 and 2 shown in FIG. 1A, terminals 1' and 2' shown in FIG. 1B) and contacts with an acupuncture point of a human body to obtain a capacitance value CH of the acupuncture point; an internal oscillator 120, which generates a predetermined oscillation frequency; an electronic counter 130, which is connected to the internal oscillator and calculates an internal oscillation frequency; an external interrupt service routine (ISR) 140, which is connected to the electronic counter and when the contact head contacts with an acupuncture point of a human body and the external interrupt service routine (ISR) receives an acupuncture point frequency signal from the contacted human body, the external interrupt service routine (ISR) calculates, in combination with the internal oscillation frequency, a frequency F2 of the contacted acupuncture point of the human body, using mathematical formula shown as follows:

$$F2 = \frac{1}{2\sqrt{L1 \times (C2 + CH)}};$$

$$F1 = \frac{1}{2\sqrt{L1 \times C2}},$$

wherein F1 is an internal oscillation frequency of the internal oscillator, L1 and C2 are oscillatory elements of the internal oscillator, and CH is a capacitance value of the acupuncture point of the human body.

Figure 3:
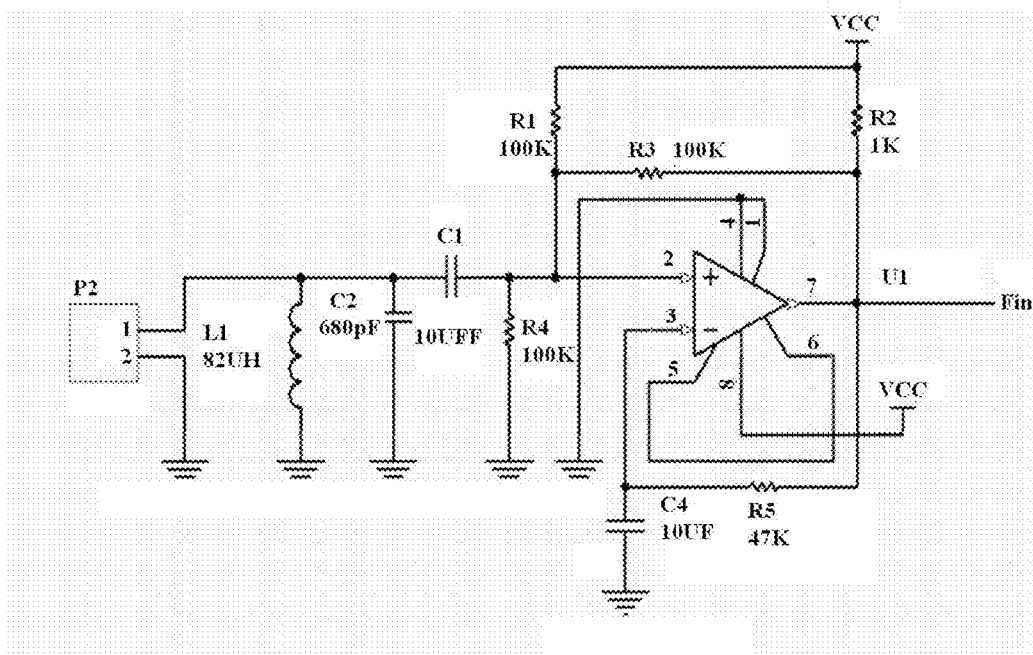
FIG. 3 shows a circuit diagram of a detecting head device for capacitively measuring an acupuncture point frequency of a human body.

FIG. 3 shows a circuit diagram of a detecting head device of the present invention, P2 is a human body measurement point; an oscillatory circuit which is constructed by combining a tank circuit, which comprises C2 and L1, and a LM311 comparison circuit. According to electric circuit theories, an output frequency F1 of an oscillator can be derived from the following formula:

$$F1 = \frac{1}{2\sqrt{L1 \times C2}}$$

When P2 is set as an input point, electric charges of an acupuncture point of a human body can be seen as a small capacitor, and CH is set as a capacitance value of an acupuncture point. According to the formula used to calculate capacitors coupled in parallel, after contacting with a human body, an output frequency F2 of an oscillator can be derived from the following formula:

$$F2 = \frac{1}{2\sqrt{L1 \times (C2 + CH)}}$$

Based on the relationship between F1 and F2, the capacitance value caused by electric charges of a skin can be derived from the following formula:

$$CH = \left(\frac{F1^2}{F2^2} - 1\right) 680 \text{ pF}$$

wherein F1 is an output frequency of the detecting head device before contacting with a human body, which is approximately 700 KHZ±5% under normal conditions, and F2 is an output frequency of the detecting head device when contacting with a human body, which is approximately from 400 KHZ to 700 KHZ, depending on the physical condition of the human body. The present invention further comprises an alarm component (not shown in the figures) which generates an alarm signal, such as a sound signal or a light signal, when (F1-F2)>500 HZ is detected, which means that the detecting head device has contacted with a human body. The present invention further comprises an analysis component (not shown in the figures), which is connected to the electronic counter, divides F2 ranging from 400 KHZ to 700 KHZ into 200 equal parts and analyzes according to a measured value of F2 of a human body depending upon which equal part the measured value of F2 falls within.

Before contacting with a human body, the frequency under normal conditions is approximately 700 KHZ. When being contacted with a human body, the range of the frequencies is approximately from 400 KHZ to 700 KHZ. When there are communication devices having the same frequency range in the surrounding area, they may cause interference.

When frequency signals are sent to a motherboard through RS232, they can be analyzed and quantified.

Because the contact area will affect the stabilization time of the circuit charging and discharging, when designing the mechanism, the area of the terminal 1 of the contact head (P2) should be expanded as much as possible, i.e. the area of the terminal 1 is bigger than the area of the terminal 2 (grounded end) to accelerate the steady speed. The contact areas of the two terminals 1' and 2', of course, can also be same (shown in FIG. 1B).

Further, the structure comprises an external interrupt service routine (ISR) of an integrated circuit (e.g. model number STM32F103C8T6), an electronic counter, an internal oscillator (an internal frequency generating module). The electronic counter is configured as follows: when turning on a power supply, the internal oscillator with a predetermined frequency will be activated, output signals are connected to a counter, allows the counter to keep counting, and when a frequency signal is inputted, the external interrupt service routine (ISR) is activated.

The function of the external interrupt service routine (ISR) is to read out a numerical value in the counter, together with the frequency of the internal oscillator, to determine a numerical value of the input frequency signal. To avoid errors caused by instantaneous contacts, the first and the final data are automatically abandoned. To avoid errors, frequency samples are taken by this system 10 times per second, and a total sampling time is 3 seconds.

When the contact head contacts with the skin, electric characteristics of the skin will change the frequency of the detecting head device; when a frequency change is detected by a controller, a recording program is activated to start the measurements.

The recorded program language is as follows:

```
j=INPUTCLK;        // the number of triggers per time unit
    INPUTCLK=0;
    if(j<(OF-80))
    {
        if(j>4550)
        {
            j=j-(4000+(OF%500));
            value=j/30;
        }
        else
        {
            value=201;
        }
    }
```

It should be noted that the highest frequency of an input signal should not be more than half of the frequency of the internal oscillator, otherwise the accuracy of the calculation of the frequency will be compromised. The highest frequency of the detecting head device used by this system is 700 KHZ and the highest frequency of the internal oscillator may be 36 MHZ, which are in conformity with the principle.

In addition, as shown in FIG. 2, the detecting head device 100 for capacitively measuring the frequency of an acupuncture point of a human body further comprises a human body contacting sensor 150, which is connected to an external interrupt service routine (ISR) 140 and generates a trigger signal when contacting with a human body to activate the external interrupt service routine (ISR) to start calculating.

What is claimed:

1. A detecting head device for capacitively measuring an acupuncture point frequency of a human body, comprising:
    a contact head, which comprises a first terminal (1,1') that contacts with an acupuncture point (P2) of the human body to obtain a capacitance value CH of the acupuncture point (P2) and a second, terminal (2,2') that is grounded;
    an internal oscillator, which comprises an inductor L1 and a capacitor C2, and is configured to generate oscillations of a predetermined internal oscillation frequency F1 when the contact head does not contact the acupuncture point (P2) of the human body, and to generate oscillations of an oscillation frequency F2 when the contact head contacts the acupuncture point (P2) of the human body;
    an electronic counter, which is connected to the internal oscillator and is configured to calculate the internal oscillation frequency F1; and
    an external interrupt service routine (ISR), being connected to the electronic counter, in which when the contact head contacts with the acupuncture point (P2) of the human body, the external ISR-receives an acupuncture point frequency signal of the contacted human body and calculates, in combination with the internal oscillator producing the oscillation, a frequency F2 of the contacted acupuncture point of the human body based on the capacitance value CH of the acupuncture point (P2) of the human body as well as an inductance value of the inductor L1 and a capacitance value of the capacitor C1 of the internal oscillator, using mathematical formulas shown as follows:

$$F1 = \frac{1}{2\sqrt{L1 \times C2}},$$

and $$F2 = \frac{1}{2\sqrt{L1 \times (C2 + CH)}}$$

wherein the inductor L1 and the capacitor C2 are oscillatory elements of the internal oscillator.

2. The detecting head device of claim 1, which further comprises a human body contacting sensor, which is connected to the external ISR and is configured to generate a trigger signal when contacting with the human body to activate the electronic counter to start counting and calculating via the external ISR module.

3. The detecting head device of claim 1, wherein the internal oscillation frequency F1 is 700 KHZ±5%, and the oscillation frequency F2 is in a range from 400 KHz to 700 KHz.

4. The detecting head device of claim 1, wherein the external (ISR) further comprises an alarm component which generates an alarm signal when a difference of the internal oscillation frequency F1 and the oscillation frequency F2 above 500 Hz is detected.

5. The detecting head device of claim 3, which further comprises an analysis component which is connected to the electronic counter, and is configured to divide the range of the oscillation frequency F2 into 200 equal parts and is configured to analyze according to a measured value of the oscillation frequency F2 of the human body depending upon which equal part the measured value of the oscillation frequency F2 falls within.

6. The detecting head device of claim 1, wherein the internal oscillator, the electronic counter, and the external (ISR) are integrated in an integrated circuit.

7. The detecting head device of claim 1, wherein a highest value of the oscillation frequency F2 is 700 KHz and a highest frequency value of the internal oscillator is 36 MHz.

8. The detecting head device of claim 1, wherein the oscillation frequency of the acupuncture point (P2) of the human body is not more than half of the oscillation frequency of the internal oscillator.

9. The detecting head device of claim 1, wherein, an area of the second terminal (2, 2') in the contact head is larger than or equal to an area of the first terminal (1, 1').

10. The detecting head device of claim 1, wherein frequency samples of the input oscillation frequency of the acupuncture point (P2) are taken by the external (ISR) 10 times per second, and a total sampling time is 3 seconds.

* * * * *